United States Patent [19]

Dreier et al.

[11] Patent Number: 5,601,543
[45] Date of Patent: Feb. 11, 1997

[54] ABSORBENT ARTICLE HAVING A SELECTIVELY WEAKENED POCKET CUFF

[75] Inventors: Kimberly A. Dreier, Cincinnati; Donald C. Roe, West Chester, both of Ohio

[73] Assignee: The Proctor & Gamble Company, Cincinnati, Ohio

[21] Appl. No.: 349,776

[22] Filed: Dec. 6, 1994

[51] Int. Cl.$^6$ .................................................. A61F 13/15
[52] U.S. Cl. .......................................... 604/385.1
[58] Field of Search ............................ 604/385.1, 385.2

[56] References Cited

U.S. PATENT DOCUMENTS

| | | | |
|---|---|---|---|
| 3,930,501 | 1/1976 | Schaar | 128/287 |
| 3,951,150 | 4/1976 | Schaar | 128/287 |
| 3,990,450 | 11/1976 | Schaar | 128/287 |
| 4,662,877 | 5/1987 | Williams | 604/385 A |
| 4,738,677 | 4/1988 | Foreman | 604/385 R |
| 4,743,246 | 5/1988 | Lawson | 604/385 A |
| 4,790,840 | 12/1988 | Cortina | 604/385.1 |
| 4,808,177 | 2/1989 | Desmarais et al. | 604/385.1 |
| 4,816,025 | 3/1989 | Foreman | 604/385.2 |
| 4,892,536 | 1/1990 | Desmarais et al. | 604/385.2 |
| 4,895,568 | 1/1990 | Enloe | 604/385.2 |
| 4,938,755 | 7/1990 | Foreman | 604/385.2 |
| 4,990,147 | 2/1991 | Freeland | 604/385.2 |
| 5,026,363 | 6/1991 | Pratt | 604/385.1 |
| 5,026,364 | 6/1991 | Robertson | 604/385.1 |
| 5,037,416 | 8/1991 | Allen et al. | 604/385.1 |
| 5,074,854 | 12/1991 | Davis | 604/385.2 |
| 5,085,654 | 2/1992 | Buell | 604/370 |
| 5,087,255 | 2/1992 | Sims | 604/385.1 |
| 5,151,092 | 9/1992 | Buell et al. | 604/385.2 |
| 5,171,236 | 12/1992 | Dreier et al. | 604/369 |
| 5,176,672 | 1/1993 | Bruemmer et al. | 604/385.1 |
| 5,187,817 | 2/1993 | Zolner | 2/400 |
| 5,207,663 | 5/1993 | McQueen | 604/385.1 |
| 5,304,159 | 4/1994 | Tanji et al. | 604/385.2 |
| 5,304,160 | 4/1994 | Igaue et al. | 604/385.2 |
| 5,344,516 | 9/1994 | Tanji et al. | 156/164 |
| 5,407,438 | 4/1995 | Hedlund et al. | 604/385.2 |
| 5,429,632 | 7/1995 | Tanji et al. | 604/385.2 |

FOREIGN PATENT DOCUMENTS

| | | |
|---|---|---|
| 0433951A2 | 6/1991 | European Pat. Off. . |
| 0486006A2 | 5/1992 | European Pat. Off. . |
| 3-218751 | 9/1991 | Japan . |
| 2159693 | 12/1985 | United Kingdom . |
| 2174591 | 11/1986 | United Kingdom . |
| 2265550 | 10/1993 | United Kingdom . |

Primary Examiner—Michael J. Milano
Attorney, Agent, or Firm—Gerry S. Gressel; Larry L. Huston; E. Kelly Linman

[57] ABSTRACT

A disposable diaper having a waist pocket cuff is disclosed. The pocket cuff has first and second portions separable along a predetermined line of weakness. The predetermined line of weakness can comprise a line of spaced apart perforations.

15 Claims, 3 Drawing Sheets

ABSORBENT ARTICLE HAVING A SELECTIVELY WEAKENED POCKET CUFF

FIELD OF THE INVENTION

The present invention relates to absorbent articles such as disposable diapers, and more particularly, to absorbent articles having a fetal containment pocket cuff.

BACKGROUND OF THE INVENTION

The major function of absorbent articles such as disposable diapers and incontinence briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist. Fecal material that is not absorbed by the absorbent article can work its way past the gaps in the article in the legs or waist of the wearer.

Contemporary disposable diapers have a topsheet, a backsheet, an absorbent core, and elasticized leg or gasket cuffs generally formed from an elastic member enclosed between portions of the topsheet and backsheet which extend beyond the edges of the absorbent core. These elasticized leg or gasket cuffs present a barrier between the edge of the diaper and the wearer's contacting clothing, and in addition, provide a gasketing action about the legs of the wearer to maintain a seal about the leg and minimize gapping.

Disposable diapers may also be provided with barrier cuffs which inhibit fecal material or gushes of urine or liquids from soiling the wearer's clothing. The barrier cuffs restrain the free flow of this material to hold such material within the diaper. U.S. Pat. No. 4,743,246 issued May 10, 1988, to Lawson discloses an absorbent article having gasket and barrier cuffs.

Disposable diapers having an opening formed in a topsheet are disclosed in the following references: GB Application 2,265,550A published Oct. 6, 1993 in the name of Tanji et al.; U.S. Pat. No. 5,176,672 issued Jan. 5, 1993 to Bruemmer et al.; U.S. Pat. 5,304,159 issued Apr. 19, 1994 to Tanji et al.; and U.S. Pat. No. 5,304,160 issued Apr. 19, 1994 to Igaue et al.

Disposable diapers may also have pockets or waistcaps for reducing the leakage of body exudates from the diaper waist region. Examples of such diapers are disclosed in U.S. Pat. No. 4,738,677 issued Apr. 19, 1988, to Foreman, and U.S. Pat. No. 5,026,364 issued Jun. 25, 1991, to Robertson.

Typically, it is desirable to dispose of waste material held in fetal containment pockets prior to discarding the used disposable absorbent article. For instance, it is desirable to empty the fecal material held in the pocket of a disposable diaper into a toilet prior to disposing of the used diaper in a waste receptacle. However, it can be difficult to scrape or otherwise remove the fecal material from the pocket.

Above referenced GB Application 2,265,550A to Tanji et al. discloses a diaper having a second nonwoven topsheet overlying a first topsheet. The second topsheet has an opening for receiving fecal material. The opening has an edge elasticized by first and second elastic members. The first and second elastic members are not continuous with each other, so that, allegedly, the second topsheet can be torn at a guide notch on the edge of the opening to expose the first topsheet. Fecal material clinging to the first topsheet is said to be exposed for removal. Tanji et al. also teaches orienting the fibers of the second topsheet in a direction along which the second topsheet is to be torn at the guide notch.

The arrangement shown in Tanji has the disadvantage that it can be difficult to tear a nonwoven. If the entire sheet of a nonwoven is weakened, such as by orienting the fibers in the longitudinal direction, the nonwoven sheet may be accidentally torn somewhere other than in the intended location, or prior to removal of the diaper from the wearer, thereby destroying the containment ability of the absorbent article. Another disadvantage of such an arrangement is that multiple, discontinuous elastic members are required to permit tearing of the second topsheet at the edge of the opening. Also, tearing of a sheet of material, once initiated, can be difficult to control, and can progress along different paths or directions. Accordingly, the second topsheet may be torn in a manner that does not permit ready removal of the fecal material.

Therefore, it is an object of the present invention to provide an absorbent article which has improved containment characteristics.

It is an additional object of the present invention to provide an absorbent article having a pocket cuff which is separable along a predetermined line of weakness for facilitating removal of waste held in the pocket cuff.

It is also an object of the present invention to provide an absorbent article having a pocket cuff which is separable along a line of spaced apart perforations.

These and other objects of the invention will be more readily apparent when considered in reference to the following description and when taken in connection with the accompanying drawings.

SUMMARY OF THE INVENTION

A disposable absorbent article, such as a diaper, is provided with a liquid pervious topsheet; a liquid impervious backsheet joined to the topsheet; an absorbent core positioned intermediate the topsheet and the backsheet; and a pocket cuff joined to the disposable absorbent article to overlie a portion of the topsheet and form a pocket recess therebetween. The pocket cuff has an open edge having laterally spaced apart open edge ends. The pocket cuff open edge can include an elastic element. A first portion of the pocket cuff is separable from a second portion of the pocket cuff along a predetermined line of weakness.

The pocket cuff includes a predetermined line of weakness which can include a generally laterally extending section spaced longitudinally from the open edge of the pocket cuff. The pocket cuff can be separated along the predetermined line of weakness to empty fecal material from the pocket cuff recess without the need to severe the open edge elastic element. In one preferred embodiment, the pocket cuff is perforated at spaced intervals to provide the predetermined line of weakness.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to articles which absorb and contain body exudates and more specifically refers to articles which are placed against or in proximity to the body of the wearer to absorb and contain the various exudates discharged from the body. Absorbent articles are typically differentiated by whether they are reusable or disposable. The term "disposable absorbent article" refers to articles which are intended to be discarded after a single use (i.e., they are not intended to be laundered or otherwise restored or reused). The absorbent articles of the present invention are preferably disposable absorbent articles. The absorbent articles may be further defined by whether they are "unitary" such that they do not require separate manipulative pans or whether they comprise an element of a diaper system such as a separate holder and liner. The absorbent articles of the present invention are preferably unitary. As used herein, the term "diaper" refers to a garment generally worn by infants and incontinent persons that is worn about the lower torso of the wearer. It should be understood, however, that the present invention is also applicable to other disposable absorbent articles such as incontinence briefs or undergarments, disposable training pants, diaper holders, sanitary napkins, and the like.

Figure 1:
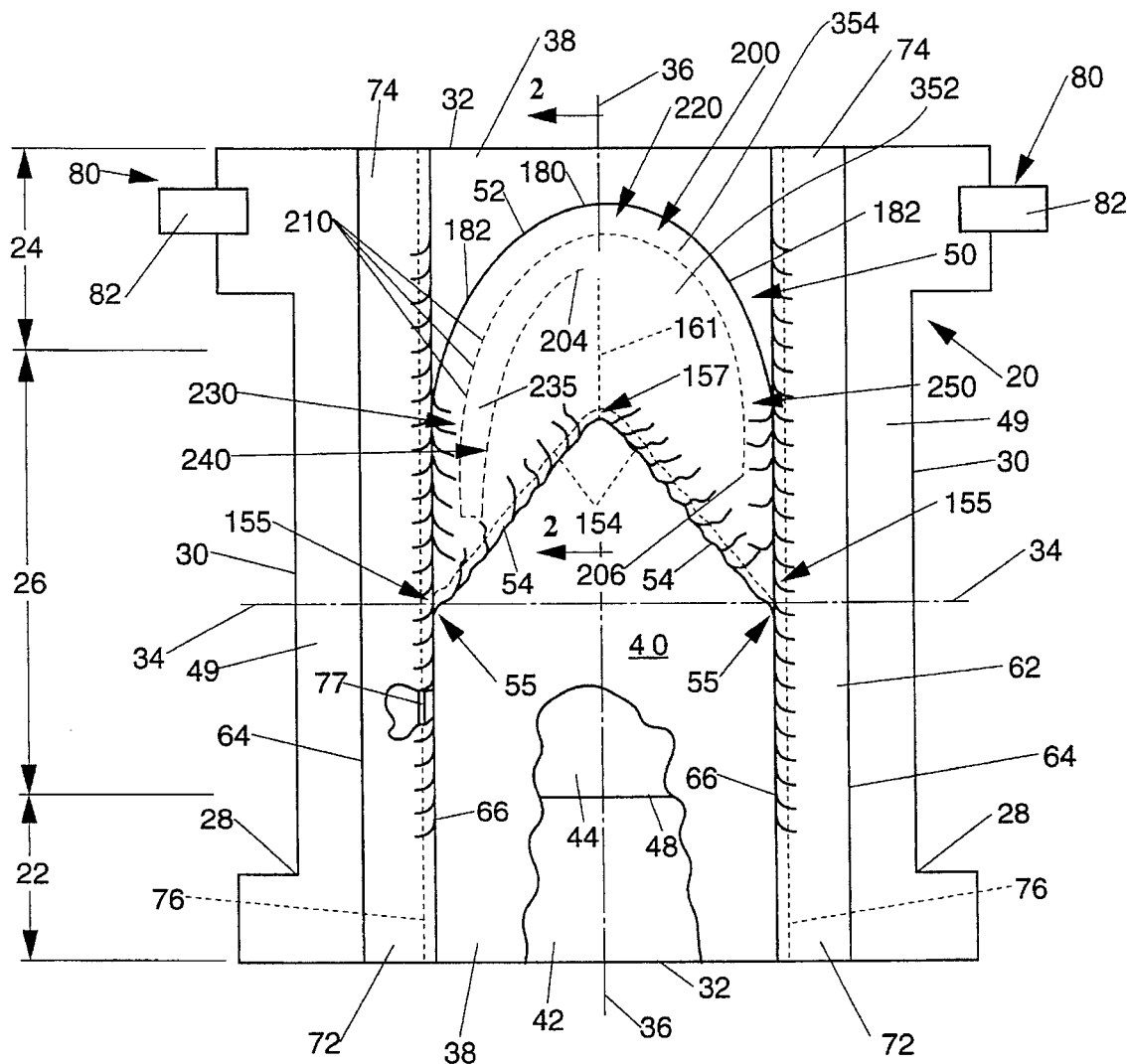
FIG. 1 is a top plan view of a disposable diaper shown partially cutaway and having a pocket cuff perforated to permit emptying of the pocket cuff recess without severing the pocket cuff open edge.

FIG. 1 is a top plan view of a diaper 20 with the portion of the diaper 20 which contacts the wearer facing the viewer. The diaper 20 shown in FIG. 1 has a first front waist region 22, a second rear waist region 24, a crotch region 26 disposed between the front and rear waist regions 22, 24, and a periphery 28 which is defined by longitudinal edges 30 and front and rear end edges 32. The diaper 20 additionally has a lateral centerline 34 and a longitudinal centerline 36.

Figure 2:
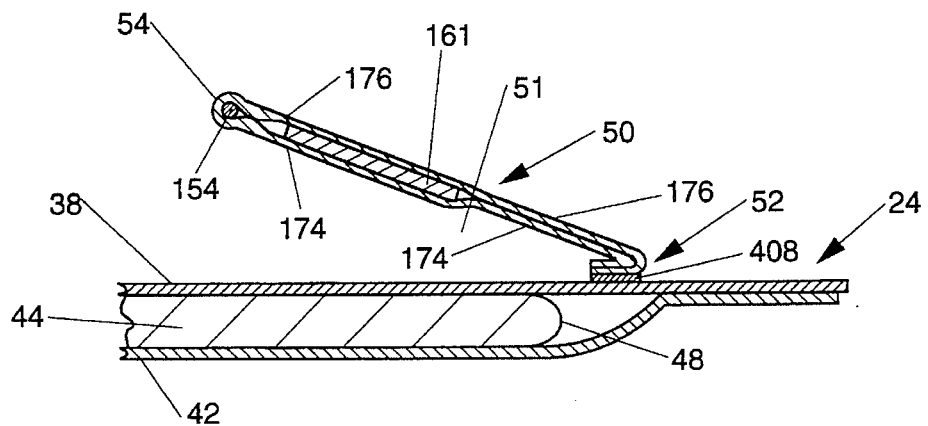
FIG. 2 is a cross-sectional view taken along lines 2—2 in FIG. 1.

FIG. 2 is a fragmentary cross-sectional view taken along section line 2—2 in FIG. 1. Referring to FIGS. 1 and 2, the diaper 20 comprises a liquid pervious topsheet 38, the liquid receiving surface of the diaper 20 being generally defined by the topsheet 38 and being designated 40; a liquid impervious backsheet 42 joined to the topsheet 38; and an absorbent core 44 positioned intermediate the topsheet 38 and the backsheet 42. The absorbent core 44 has side edges (not shown) and front and rear waist edges 48. The diaper 20 also includes a marginal side flap 49 extending laterally outward from each side edge of the absorbent core 44 in at least the crotch region 26.

The diaper 20 further includes a pocket cuff 50 overlying a portion of the topsheet 38. The pocket cuff 50 has a closed edge 52 which can be juxtaposed with the rear waist region 24, and an open edge 54 extending between laterally spaced apart open edge ends 55. The open edge 54 can have an apex 157 positioned substantially on the longitudinal centerline 36, and the open edge 54 can include an elastic member 154. In one embodiment the pocket cuff 50 can include a longitudinally extending elastic member 161 for aiding in forming the apex 157. Allowed U.S. patent application Ser. No. 08/075,205, Absorbent Article Having a Pocket Cuff, filed Jun. 10, 1993, and U.S. patent application Ser. No. 08/302,569, Absorbent Article Having a Pocket Cuff with an Apex, filed Sep. 8, 1994, are incorporated herein by reference for the purpose of showing pocket cuff constructions.

The pocket cuff 50 and the topsheet 38, together, define a fetal containment pocket recess 51 therebetween, as shown in FIG. 2. In order to facilitate removal of fecal material from the pocket recess 51, the pocket cuff 50 is provided with at least one predetermined line of weakness 200. A first portion 352 of the pocket cuff 50 is separable from a second portion 354 of the pocket cuff 50 along the predetermined line of weakness 200. The line of weakness 200 can comprise one or more straight segments, curved segments, or combinations of straight and curved segments.

In the embodiment shown in FIG. 1, the line of weakness 200 comprises a line of spaced apart perforations 210 formed in the pocket cuff 50. The first and second portions 352 and 354 of the pocket cuff 50 can be separated by tearing along the line of perforations 210, thereby permitting emptying of the pocket recess 51 prior to disposal of the diaper 20.

The diaper 20 can include a barrier cuff 62 joined to each of the side flaps 49. The pocket cuff open edge 54 extends between open edge ends 55. Each end 55 is joined to a respective barrier cuff 62. In FIG. 1, a portion of each barrier cuff 62 extends longitudinally rearward from a respective open edge end 55. A portion of each barrier cuff 62 also extends longitudinally forward from a respective open edge end 55.

The diaper 20 preferably includes a "dual tension fastening system" as disclosed in U.S. Pat. No. 5,151,092, issued to Buell et al. on Sep. 29, 1992. A dual tension fastening system can include fastening means 80 for securing the diaper on the wearer, such as a pair of tape tab fasteners 82 disposed in the rear waist region 24. Suitable fastening means 80 include but are not limited to adhesive fasteners and mechanical fasteners. U.S. Pat. No. 5,151,092 is incorporated herein by reference to show the construction of such a dual tension fastening system.

Examining the individual components of the diaper 20 in more detail, the backsheet 42 can have length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the longitudinal edges 30 and the end edges 32 in the front and rear waist regions 22 and 24. As shown in FIG. 1, the topsheet 38 is generally coterminous with the backsheet 42 along at least the end edges 32 and the longitudinal edges 30. U.S. Pat. No. 3,860,003, issued to Buell on Jan. 14, 1975 and above referenced U.S. Pat. No. 5,151,092 are incorporated herein by reference for the purpose of showing such diaper configurations. In an alternative embodiment, the topsheet 38 may have length or width dimensions generally smaller than those of the backsheet 42.

The topsheet 38 and the backsheet 42 can extend beyond the side edges of the absorbent core 44 to form the side flap 49. The topsheet 38 and backsheet 42 also can extend beyond the waist edges 48 of the absorbent core 44 in front and rear waist regions 22 and 24. Front and rear waist regions 22 and 24 can include a waist region elastic feature (not shown) for providing lateral expansion of at least a portion of the from and rear waist regions 22 and 24. Above referenced U.S. Pat. No. 5,151,092 is incorporated herein by reference to show the construction of a suitable waist region elastic feature.

The absorbent core 44 may be any means which is generally compressible, conformable, non-irritating to the wearer's skin, and capable of absorbing and retaining liquids and certain body exudates. The absorbent core 44 may be manufactured in a wide variety of sizes and shapes including, but not limited to, rectangular, hourglass, asymmetric, and T-shaped. The absorbent core 44 can be manufactured from a wide variety of liquid absorbent materials commonly used in disposable diapers and other absorbent articles, such as comminuted wood pulp which is generally referred to as airfelt.

Examples of other suitable absorbent materials include creped cellulose wadding, absorbent foams, absorbent sponges, super absorbent polymers, absorbent gelling materials, or any equivalent materials or combination of materials. The total absorbent capacity of the absorbent core 44 should, however, be compatible with the design exudate loading in the intended use of the diaper 20. Further, the size and absorbent capacity of the absorbent core 44 may be varied to accommodate wearers ranging from infants through adults.

The absorbent core 44 may comprise a layer of absorbent material comprising hydrophilic fibers and particles of absorbent gelling material (hydrogel). The following patents are incorporated by reference for the purpose of showing suitable constructions and materials for the absorbent core 44: U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,888,321 issued Dec. 19, 1989 to Angstadt; and U.S. Pat. No. 5,147,345 issued Sep. 15, 1992 to Young et al.

The backsheet 42 is positioned adjacent the absorbent core 44 and can be secured thereto by core attachment means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Century Adhesives, Inc. of Columbus, Ohio and marketed under the trade name Century 5227; and by H. B. Fuller Company of St. Paul, Minn. and marketed as HL-1258. The core attachment means can comprise an open pattern network of filaments of adhesive as is shown in U.S. Pat. No. 4,573,986 issued to Minetola et al. on Mar. 4, 1986, and which is incorporated herein by reference. An exemplary attachment means of an open pattern network of filaments comprises several lines of adhesive filaments swirled into a spiral pattern such as is illustrated in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference for the purpose of showing suitable attachment means.

The backsheet 42 is impervious to liquids and is preferably manufactured from a thin plastic film, although other flexible liquid impervious materials may also be used. The term "flexible" refers to materials which are compliant and which will readily conform to the contours of the human body. The backsheet 42 prevents the exudates absorbed and contained in the absorbent core 44 from wetting articles which contact the diaper 20 such as bedsheets and undergarments. The backsheet 42 may comprise a woven or nonwoven material, polymer films such as thermoplastic films of polyethylene or polypropylene, or composite materials such as film coated nonwoven material. Preferably, the backsheet 42 is a thermoplastic film having a thickness of from about 0.012 mm (0.5 mil) to about 0.051 cm (2.0 mils).

Suitable materials for the backsheet include blends comprised of about 45–90% linear low density polyethylene and about 10–55% polypropylene. Exemplary films for use as the backsheet 42 of the present invention are manufactured by Tredegar Industries Inc. of Terre Haute, Indiana under the designation RR8220 blend for blown films and RR5475 blend for cast films.

The topsheet 38 is joined to the absorbent core 44 and the backsheet 42 by attachments means (not shown) such as those well known in the art. Suitable attachment means are described above with respect to joining the backsheet 42 to the absorbent core 44. As used herein, the term "joined" encompasses configurations whereby an element is directly secured to the other element by affixing the element directly to the other element, as well as configurations whereby the element is indirectly secured to the other element by affixing the element to intermediate members which in turn are affixed to the other element. In one embodiment the top sheet 38 and the backsheet 42 are joined directly to each other in at least a portion of the periphery 28 of the diaper 20, and are indirectly joined together by directly joining the topsheet 38 and the backsheet 42 to the absorbent core 44.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. The top sheet can be made of a hydrophobic material, or be treated to be hydrophobic, in order to isolate the wearer's skin from liquids in the absorbent core 44.

There are a number of manufacturing techniques which may be used to manufacture the topsheet 38. For example, the topsheet 38 may be a nonwoven web of fibers. When the top sheet 38 comprises a nonwoven web, the web may be spunbonded, carded, wet-laid, meltblown, hydroentangled, or the like. A suitable topsheet 38 can be carded and thermally bonded by means well known to those skilled in the fabric art. A suitable topsheet 38 comprises staple length polypropylene fibers having a length of at least about 15.9 mm (0.625 inch) and has a basis weight from about 14 to about 25 grams per square meter. A suitable topsheet material is manufactured by Veratec, Inc., a Division of International Paper Company, of Walpole, Mass., under the designation P-8.

Referring to FIGS. 1 each barrier cuff 62 has a proximal edge 64, a distal edge 66, a first barrier cuff end 72 positioned in the front waist region 22, and a second barrier cuff end 74 positioned in the rear waist region 24. The barrier cuff 62 further comprises a spacing means 76 operatively associated with the barrier cuff 62 for spacing the distal edge 66 apart from the topsheet 38. The spacing means 76 can comprise one or more elastic members 77 extending along the distal edge 66 of each barrier cuff, as shown in FIG. 1.

The elastic members 77 are operatively associated with the barrier cuff 62 by an attachment means, which secures the elastic members 77 to the barrier cuff 62 in an elastically contractible condition. The elastic members 77 contract or gather the distal edge 66 of the barrier cuff 62, so that the distal edge 66 is spaced away from the topsheet 38. The elastic members 77 can be made from a number of suitable materials including elastomeric films, polyurethane films, Lycra, elastomeric foams, formed elastic scrim, and elastic strands. The following U.S. Patents are incorporated by reference for the purpose of showing barrier cuff constructions: U.S. Pat. No. 5,087,255 issued Feb. 11, 1992, to Sims; U.S. Pat. No. 5,085,654 issued Feb. 4, 1992 to Buell, and U.S. Pat. No. 4,938,755 issued Jul. 3, 1990 to Foreman.

The pocket cuff 50 preferably comprises a material that is compliant, soft, and non-irritating to the wearer's skin. The pocket cuff 50 can be formed from a material that is liquid pervious or liquid impervious. A suitable pocket cuff 50 may be made from a wide range of materials, such as apertured plastic films, or woven or nonwoven o webs of natural fibers (e.g., wood or cotton fibers) or synthetic fibers (e.g., polyester polypropylene, or rayon fibers), or composites of polyolefinic films and nonwovens. Optionally, the pocket cuff 50 may formed from an elastomeric web of material. The pocket cuff 50 can be hydrophobic to isolate the wearer's skin from liquids contained in the pocket space 51 formed between the topsheet 38 and the pocket cuff 50. A suitable pocket cuff 50 comprises a web of staple length polypropylene fibers. Suitable materials from which the pocket cuff 50 can be made are manufactured by Veratec, Inc., a Division of International Paper Company, of Walpole, Mass., under the designations P-8, P-9, P-10 or P-11. Optionally, the pocket cuff 50 can comprise a gluteal groove spacer as described in U.S. patent application Ser. No. 08/302,291 filed Sep. 8, 1994 in the name of Dreier, which application is incorporated herein by reference.

Referring to FIG. 2, the pocket cuff 50 can be formed from a sheet of material, such as a nonwoven, to comprise two layers 174 and 176. The elastic element 154 and the elastic member 161 can be secured between the layers 174 and 176 in an elastically contractible manner, and the layers 174 and 176 can be bonded together by any suitable means, including but not limited to adhesive bonding means. U.S. Pat. Nos. 3,860,003 and 4,081,301 are incorporated herein by reference to show an elastic member secured to a diaper component in an elastically contractible manner.

The pocket cuff 50 in FIG. 2 comprises two layers 176 and 174. However, two layers are not necessary to the operation of the pocket cuff 50, and a suitable pocket cuff 50 can be formed having just one layer, or having more than two layers. The elastic element 154 and the elastic member 161 can be made from a number of suitable materials including elastomeric films, polyurethane films, Lycra, elastomeric foams, formed elastic scrim, and elastic strands. Optionally, the elastic element 154 and/or the elastic member 161 can comprise a laminate construction. For instance, the elastic element 154 and the elastic member 161 can comprise a laminate of an elastic film and a nonwoven. An elastic film, such as a EXX-500 film available from the Exxon Chemical Company of Lake Zurich, Ill. can be elongated about 100 percent and intermittently bonded, such as by ultra-sonic bonding, between two layers of a nonwoven material. Suitable nonwoven materials between which the elastic film can be bonded are available from Veratec, Inc. under the designations P-8, P-9, P-10, or P-11.

The pocket cuff can be joined to an underlying element of diaper 20 and the barrier cuffs 62 along the closed edge 52 to provide a seal along the closed edge 52 from one juncture 155 to the other juncture 155, thereby preventing leakage of body exudates past the rear waist region 24. The pocket cuff can be joined to topsheet 38 along closed edge 52 by an adhesive attachment means 408, as shown in FIG. 2. Alternatively, pocket cuff 50 can be joined to backsheet 42 along closed edge 52 if topsheet 38 does not extend fully into the rear waist region 24. The closed edge 52 can have a generally laterally oriented portion 180 extending between generally forward extending portions 182, as shown in FIG. 1.

The open edge 54 of the pocket cuff 50 extends between the laterally spaced apart open edge ends 55. The open edge ends 55 are joined to the barrier cuffs 62 at a pair of laterally spaced apart junctures 155, as shown in FIGS. 1. Each juncture 155 is positioned intermediate the first end 72 and the second end 74 of a barrier cuff 62.

Referring to FIG. 1, the first portion 352 of the pocket cuff 50 is separable from the second portion 354 of the pocket cuff 50 along the predetermined line of weakness 200. The predetermined line of weakness 200 has a first end 204 and a second end 206. The first and second ends 204 and 206 are spaced from the open edge 54 and the barrier cuffs 62. The predetermined line of weakness 200 in FIG. 1 comprises a generally laterally extending segment designated 220 spaced longitudinally from the open edge 54. The predetermined line of weakness 200 also includes generally longitudinally extending segments designated 230, 240 and 250. Together, the segments 220, 230, 240 and 250 provide a curvilinear path from the first end 204 to the second end 206 along which the pocket cuff 50 can be separated. It will be understood that the segments 230, 220 and 250 can be formed by making a generally straight line of perforations in the piece of material from which the pocket cuff is to be formed, and then joining the piece of pocket cuff material to the diaper 20 in such a fashion that the line of perforations is shaped (such as by the elastic forces provided by elastic element 154 and elastic member 161 ) to form a curvilinear predetermined line of weakness 200.

The longitudinally extending segments 230 and 240 can be generally parallel and closely spaced together, as shown in FIG. 1. The portion of the pocket cuff 50 between the sections 230 and 240 can be grasped, such as between the thumb and forefinger, and separated along segments 230 and 240 to form a pull tab 235. By pulling on the tab 235, one can separate the pocket cuff 50 along the remainder of the predetermined line of weakness 200. Optionally, a pull tab can be formed from a separate piece of material joined to the outer surface of a portion of the pocket cuff 50, such as between segments 230 and 240.

Figure 5:
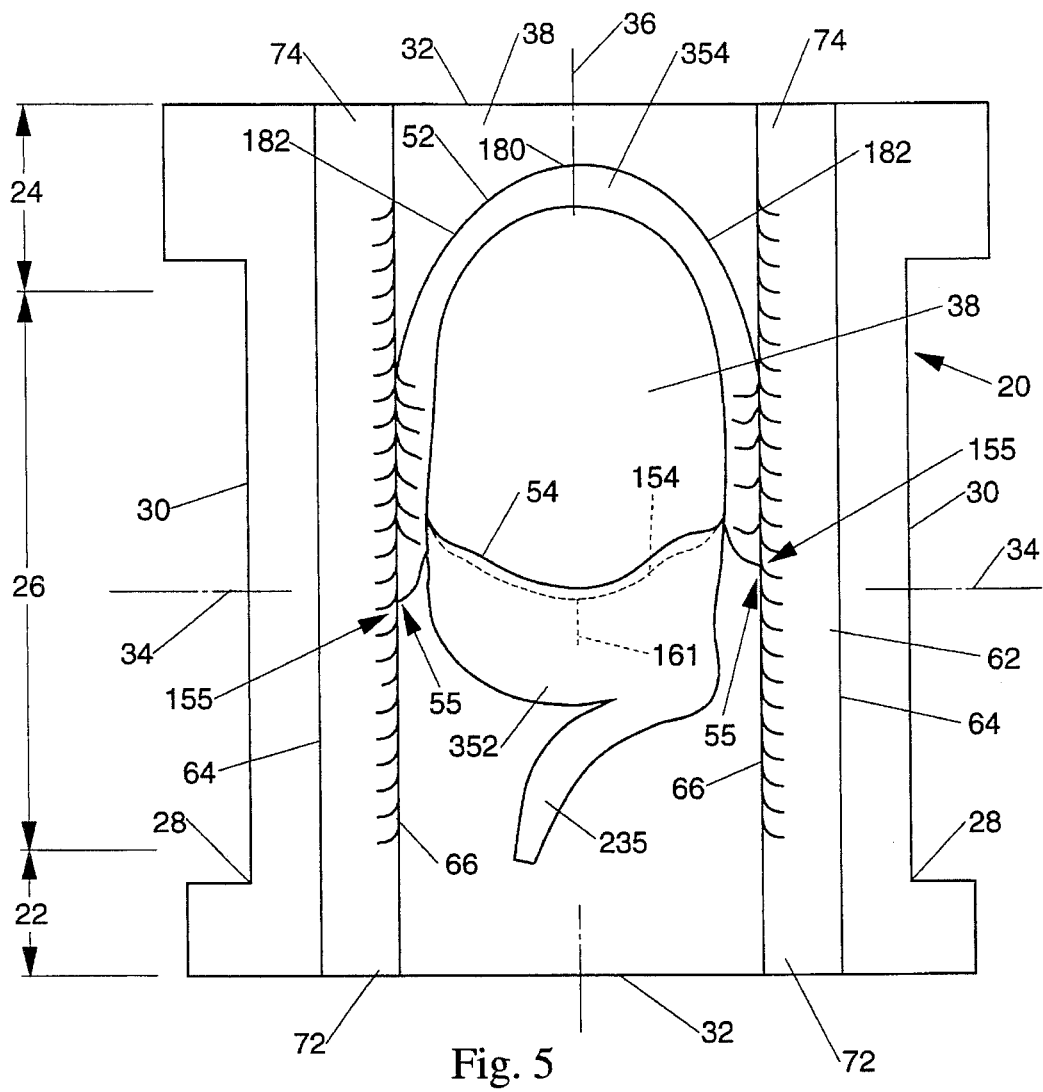
FIG. 5 is a top plan view of the disposable diaper of FIG. 1 wherein a first portion of the pocket cuff has been separated from a second portion of the pocket cuff along a predetermined line of weakness.

Referring to FIG. 5, further separation of the pocket cuff 50 along the laterally extending segment 220 and the generally longitudinally extending segment 250 permits the first portion 352 of the pocket cuff 50 to be pulled longitudinally forward with tab 235, while remaining attached to the pocket cuff 50 along the open edge 54. The first portion 352 thereby forms a flap which can be pulled forward to permit removal of fetal material from the pocket recess 51.

Spacing the ends 204 and 206 from the open edge 54 and spacing the generally laterally extending portion 220 of the predetermine line of weakness 200 from the open edge 54 provides the advantage that the pocket recess 51 can be emptied without the need to tear through the open edge 54. Accordingly, there is no need to provide discontinuities in the elastic element 154 in the open edge 54 as taught by Tanji et al.

The predetermined line of weakness 200 should be sufficiently long such that, when the pocket cuff is separated along the predetermined line of weakness, no further tearing of the pocket cuff is required to permit removal of fecal material from the recess 51. The predetermined line of weakness 200 should have a length, as measured from end 204 to end 206, which is at least about half, and preferably at least about three quarters of the distance from the open edge 54 to the closed edge 52, as measured along the longitudinal centerline 36. In FIG. 1, the length of the predetermined line of weakness 200 is greater than the distance from the open edge 54 to the closed edge 52, as measured along the longitudinal centerline 36.

The predetermined line of weakness 200 preferably comprises a plurality of spaced apart perforations 210. The perforations 210 extend through the thickness of the pocket cuff 50. In embodiments where the pocket cuff 50 comprises two or more layers, such as layers 174 and 176, the perforations 210 should extend through all the layers. The perforations 210 can have a length of about 3–5 mm and be spaced apart a distance of about 1–2 mm. A suitable perforator for making the perforations 210 is manufactured by the Ohio Knife Company of Cincinnati, Ohio.

Figure 3:
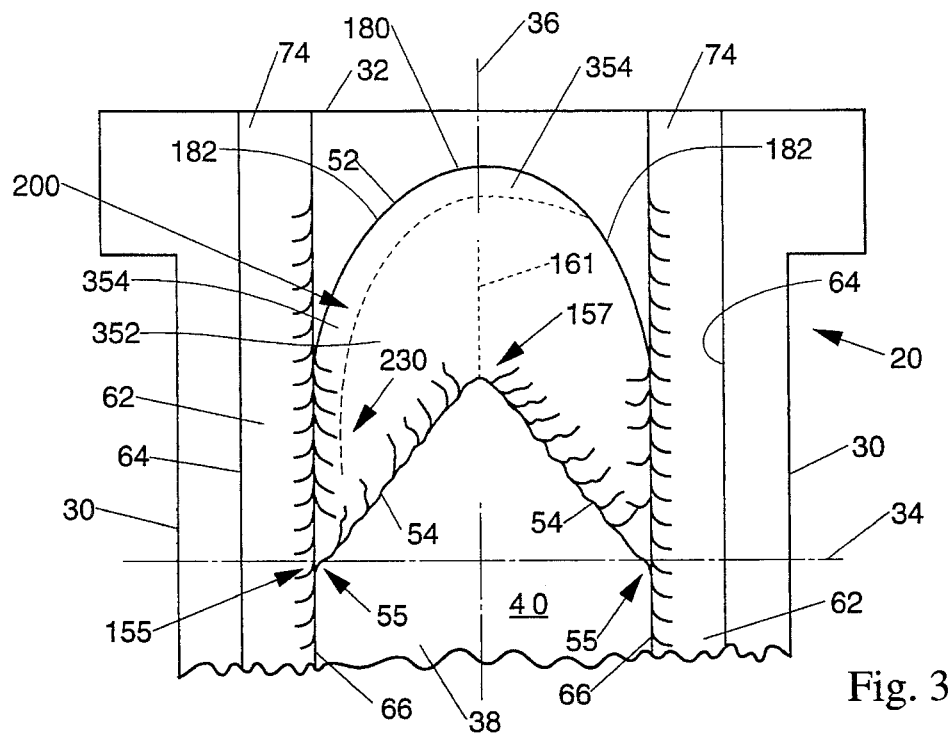
FIG. 3 is a partial top plan view of a disposable diaper having an alternative perforation pattern.

FIG. 3 shows an alternative line of weakness 200 which can be used with a pocket cuff 50 wherein the elastic element 154 is omitted from the open edge 54, or comprises discontinuous pieces of elastic. The apex 157 can be formed with a longitudinally extending elastic member 161. In FIG. 3, the predetermined line of weakness 200 comprises a generally longitudinally extending segment 230 extending rearward from the open edge 54, and a generally laterally extending segment 220. The generally laterally extending segment 220 is spaced longitudinally from the open edge 54 and positioned intermediate the closed edge 52 and the elastic member 161. The first portion 352 of the pocket cuff 50 can be separated from the second portion 354 along the predetermined line of weakness 200 to form a flap. The flap formed by the first portion 352 can be displaced laterally away from the topsheet 38 to permit removal of fecal material in the pocket recess 51.

Figure 4:
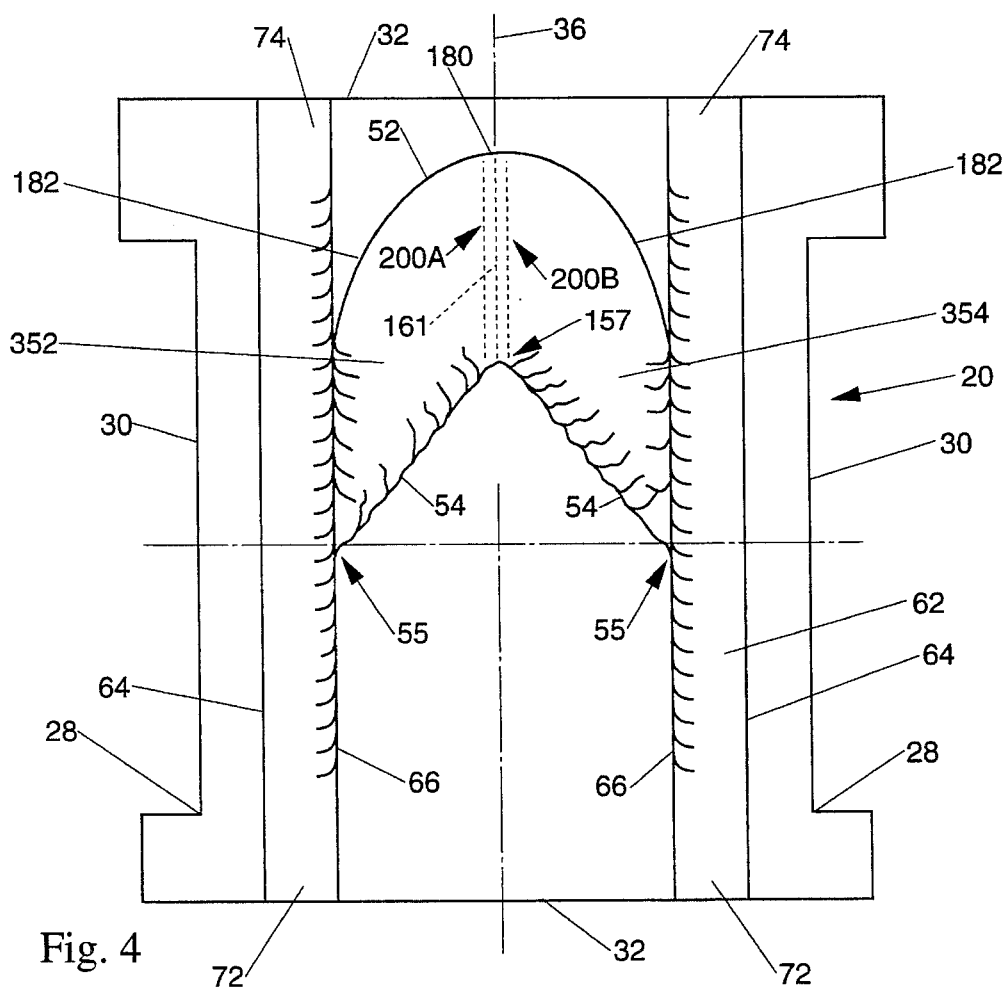
FIG. 4 is a top plan view of a disposable diaper having a pocket cuff with two longitudinally extending lines of perforations.

FIG. 4 shows another embodiment of a pocket cuff 50 according to the present invention. In FIG. 4, the pocket cuff 50 comprises two generally longitudinally extending lines of weakness 200A and 200B. In FIG. 4, the pocket cuff open edge 54 does not include an elastic element 154, or alternatively, the elastic element 154 is discontinuous at the apex 157. The apex 157 in the open edge 54 can be formed by a longitudinally extending elastic member 161 disposed intermediate the lines of weakness 200A and 200B. The lines of weakness 200A and 200B can extend longitudinally rearward from the open edge 54 to the closed edge 52. A first left half portion 352 of the pocket cuff 50 can be separated from a second right half portion 354 upon tearing the pocket cuff 50 along the lines of weakness 200A and 200B. The flaps formed by the separated half portions 352 and 354 can be displaced away from the topsheet 38 to permit removal of fecal material in the pocket recess 51. Two lines of weakness 200A and 200B are shown in FIG. 4. Optionally, one of the lines of weakness 200A or 200B could be omitted so that the elastic member 161 would remain attached to one of the first and second pocket half portions 352 and 354.

Figure 6:
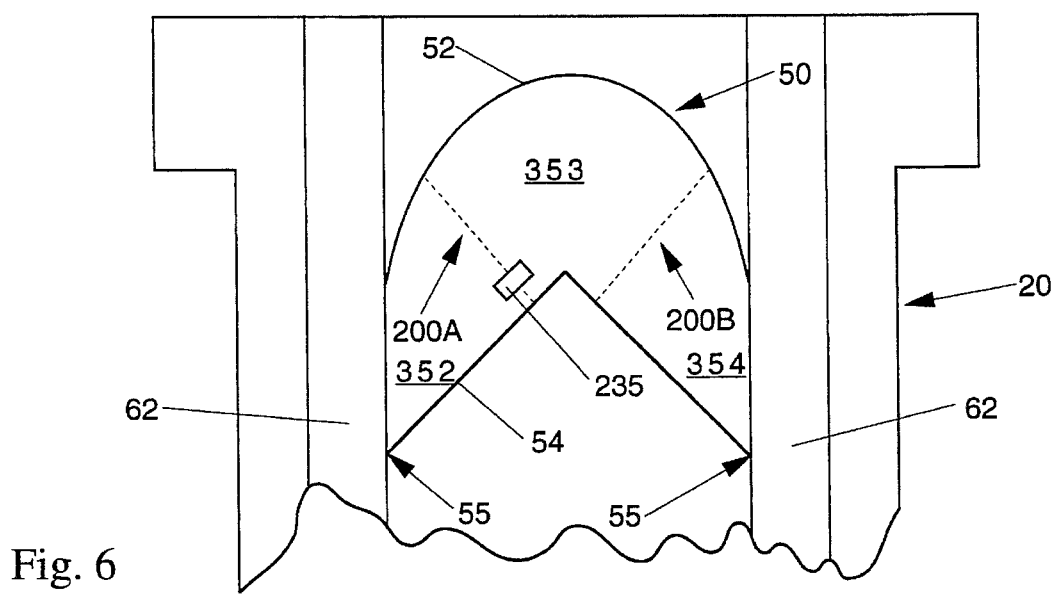
FIG. 6 is a top plan view of a disposable diaper having a pocket cuff with two diagonally extending lines of perforations.

In FIG. 6, the pocket cuff comprises diagonally extending lines of weakness 200A and 200B. Each of the lines of weakness 200A and 200B extends longitudinally and laterally from the open edge 54 of the pocket cuff 50. The diagonally extending lines of weakness 200A and 200B provide for separation of the pocket cuff 50 into three portions 352, 353 and 354 to permit easy access to material held within the recess 51.

While particular embodiment of the present invention have been illustrated and described, it would be obvious to those skill in the art that various other changes and modifications can be made without departing from the spirit and scope of the present invention. It is therefore intended to cover in the appended claims all such changes and modifications.

What is claimed is:

1. A disposable absorbent article having longitudinal edges, a front end edge, a rear end edge, a longitudinal centerline and a lateral centerline, the disposable absorbent article comprising:

a liquid pervious topsheet;

a liquid impervious backsheet joined to the topsheet;

an absorbent core positioned between the topsheet and the backsheet; and a pocket cuff joined to the disposable absorbent article to form a pocket recess, the pocket cuff having an open edge having laterally spaced apart open edge ends, and wherein a first portion of the pocket cuff is separable from a second portion of the pocket cuff along a predetermined line of weakness, and wherein the predetermined line of weakness comprises a generally laterally extending predetermined line of weakness, the generally laterally extending predetermined line of weakness being spaced longitudinally from the open edge.

2. The disposable absorbent article of claim 1 wherein the predetermined line of weakness comprises spaced apart perforations.

3. The disposable absorbent article of claim 2 wherein the pocket cuff comprises a generally laterally extending line of spaced apart perforations, and wherein the laterally extending line of spaced apart perforations is spaced longitudinally from the pocket cuff open edge.

4. The disposable absorbent article of claim 3 wherein the pocket cuff open edge comprises an elastic member.

5. The disposable absorbent article of claim 2 wherein the predetermined line of weakness comprises a generally longitudinally extending line of spaced apart perforations.

6. The disposable absorbent article of claim 2 wherein the pocket cuff comprises a pull tab for separating the first and second portions of the pocket cuff along the predetermined line of weakness.

7. The disposable absorbent article of claim 2 wherein the length of the predetermined line of weakness is at least about half the distance from the pocket cuff open edge to the pocket cuff closed edge as measured along the longitudinal centerline of the disposable absorbent article.

8. The disposable absorbent article of claim 7 wherein the length of the predetermined line of weakness is at least about three quarters of the distance from the pocket cuff open edge to the pocket cuff closed edge as measured along the longitudinal centerline of the disposable absorbent article.

9. The disposable absorbent article of claim 8 wherein the length of the predetermined line of weakness is greater than the distance from the pocket cuff open edge to the pocket cuff closed edge as measured along the longitudinal centerline of the disposable absorbent article.

10. A disposable absorbent article having longitudinal edges, a front end edge, a rear end edge, a longitudinal centerline and a lateral centerline, the disposable absorbent article comprising:

a liquid pervious topsheet;

a liquid impervious backsheet joined to the topsheet;

an absorbent core positioned between the topsheet and the backsheet;

a barrier cuff disposed adjacent each longitudinal edge of the disposable absorbent article, each barrier cuff extending longitudinally from a first barrier cuff end to a second barrier cuff end, and each barrier cuff having a proximal edge and a distal edge; and a pocket cuff positioned intermediate the barrier cuffs, the pocket cuff having an open edge, the open edge having laterally spaced apart open edge ends, each open edge end joined to a barrier cuff at a juncture positioned intermediate the first and second barrier cuff ends; and wherein the pocket cuff comprises a line of spaced apart perforations for providing separation of a first portion of the pocket cuff from a second portion of the pocket cuff, wherein the line of spaced apart perforations comprises a generally longitudinally extending line of perforations.

11. The disposable absorbent article of claim 10 wherein the pocket cuff comprises a generally laterally extending line of spaced apart perforations.

12. The disposable absorbent article of claim 10 wherein the line of perforations extends from a first end to a second end, and wherein the first and second ends of the line of perforations are spaced from the barrier cuffs and the pocket cuff open edge.

13. A disposable absorbent article having longitudinal edges, a front end edge, a rear end edge, a longitudinal centerline and a lateral centerline, the disposable absorbent article comprising:

a liquid pervious topsheet;

a liquid impervious backsheet joined to the topsheet;

an absorbent core positioned between the topsheet and the backsheet;

a barrier cuff disposed adjacent each longitudinal edge of the disposable absorbent article, each barrier cuff extending longitudinally from a first barrier cuff end to a second barrier cuff end, and each barrier cuff having a proximal edge and a distal edge; and a pocket cuff positioned intermediate the barrier cuffs, the pocket cuff having an open edge, the open edge having laterally spaced apart open edge ends, each open edge end joined to a barrier cuff at a juncture positioned intermediate the first and second barrier cuff ends; and wherein the pocket cuff comprises a plurality of lines of spaced apart perforations for providing separation of a first portion of the pocket cuff from a second portion of the pocket cuff.

14. The disposable absorbent article of claim 13 wherein the pocket cuff comprises a pair of generally parallel, generally longitudinally extending lines of spaced apart perforations.

15. The disposable absorbent article of claim 13 wherein the pocket cuff comprises a pair of generally longitudinally and laterally extending lines of spaced apart perforations.

* * * * *

UNITED STATES PATENT AND TRADEMARK OFFICE
CERTIFICATE OF CORRECTION

PATENT NO. : 5,601,543
DATED : February 11, 1997
INVENTOR(S) : Kimberly A. Dreier et al.

It is certified that error appears in the above-indentified patent and that said Letters Patent is hereby corrected as shown below:

| | |
|---|---|
| Column 1, line 8 | delete "fetal" and insert --fecal--. |
| Column 3, line 38 | delete "pans" and insert --parts--. |
| Column 4, line 16 | delete "fetal" and insert --fecal--. |
| Column 8, line 61 | delete "fetal" and insert --fecal--. |
| Column 9, line 56 | delete "fight" and insert --right--. |

Signed and Sealed this

Twenty-fourth Day of June, 1997

Attest:

BRUCE LEHMAN

*Attesting Officer*          *Commissioner of Patents and Trademarks*